United States Patent [19]

Godtfredsen et al.

[11] Patent Number: 4,859,589

[45] Date of Patent: Aug. 22, 1989

[54] ENZYMATIC METHOD FOR PREPARATION OF EPOXY COMPOUNDS

[75] Inventors: Sven E. Godtfredsen, Vaerlose, Denmark; Fredrik Bjorkling, Helsingborg, Sweden

[73] Assignee: Novo Industri A/S, Bagsvaerd, Denmark

[21] Appl. No.: 121,918

[22] Filed: Nov. 17, 1987

[30] Foreign Application Priority Data

Nov. 18, 1986 [DK] Denmark .............................. 5498/86

[51] Int. Cl.⁴ ....................... C07H 15/26; C12P 19/58
[52] U.S. Cl. ......................................... 435/73; 435/74; 435/77; 435/96; 435/98; 435/100
[58] Field of Search ....................... 435/73, 74, 77, 96, 435/98, 100

[56] References Cited

U.S. PATENT DOCUMENTS 3,133,856  5/1964  Neely .................................... 435/74

FOREIGN PATENT DOCUMENTS 0268461  5/1988  European Pat. Off. .............. 435/77

OTHER PUBLICATIONS

CA88(191271p), Paulsen et al, Chem Ber, 1978, 111(3)879-89.

Primary Examiner—Herbert J. Lilling
Attorney, Agent, or Firm—Morris Fidelman; Franklin D. Wolffe

[57] ABSTRACT

An epoxy group in a molecule can enzymatically be transferred to another molecule, thereby synthesizing carbohydrates carrying an epoxy group in the aglycone position.

11 Claims, No Drawings

ENZYMATIC METHOD FOR PREPARATION OF EPOXY COMPOUNDS

The present invention relates to a method for preparation of a carbohydrate carrying an epoxy residue as an glucosidic aglycone or otherwise stated a method for preparation of an epoxy substituted aldose or ketose sugar.

INTRODUCTION

Epoxides constitute a class of organic compounds of great practical importance as intermediates in organic syntheses and as a class of compounds which per se exhibits many useful properties. Accordingly, many methods have during the years been designed for synthesis of epoxides as described in major textbooks of organic chemistry as e.g. in Comprehenisve Organic Chemistry edited by Barton and Ollis and published by Pergamon Press, 1984. Basically two major methods are used for synthesis of a given target molecule containing an epoxy group: Either the epoxy group is generated from proper fractional groups present in a precursor of the target molecule such as a group containing a carbon-carbon double bond or the epoxide is introduced into the target molecule by a condensation reaction, in which one of the reactants carries an epoxy group. The present invention is of the latter kind.

BACKGROUND OF THE INVENTION

One major difficulty met in organic synthesis of epoxides stems from the reactivity of the epoxy group. Under a wide variety of conditions, epoxides will react with solvents and a large number of organic functional groups, one consequence being that introduction of an epoxy group into a complex, polyfunctional organic molecule can be an exceedingly difficult if not an impossible task.

One example of this kind relates to carbohydrate molecules carrying an epoxy group in the glucosidic aglycone, c.f. formula I.

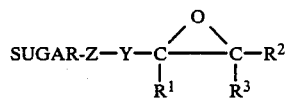

(I)

Due to the presence in such molecules of many reactive groups, the low solubility of the compounds in most organic solvents and the fragile character of the molecules it is a difficult and often quite lengthy task to prepare such compounds by organic synthesis. One example described by J. E. G. Barnett and A. Ralph in Carbohydr. Res. 17 (1971), 231, relates to synthesis of 2,3-epoxypropyl-$\beta$-D-glucopyranoside of formula II.

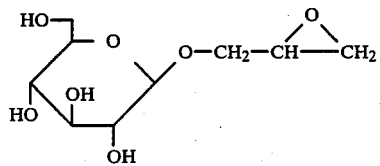

(II)

Synthesis of sugar molecules carrying an epoxy group comprises a rather long sequence of synthetic steps from readily available starting materials.

In recent years there has been a growing awareness in regard to the potential of enzymes as organic catalysts. As these catalysts are unique in many respects they are potentially very useful in organic synthesis. For example, the enzymes open up the possibility of performing organic reactions under exceedingly mild conditions, and they are often substrate selective, whereby for example selective conversion of a single group among several chemically very similar groups in organic molecules or synthesis of optically pure organic components from racemic starting materials is made possible.

One group of enzymes which have attracted some interest as organic catalysts are enzymes capable of splitting bonds at the C-1 position (aldoses) or C-2 position (ketoses) of a carbohydrate. These enzymes have attracted the interest of organic chemists due to the possibility of performing some chemical reactions at the enzymatic cleaving sites.

The use of $\beta$-galactosidases for synthesis of galactosides illustrates how enzymes, which are able to split bonds at the C-1 position (aldoses) or C-2 position (ketoses) of carbohydrates can be utilized for organic synthesis. Thus, in J. Biol. Chem. 248 (1973), 6571–6574, T. J. Silhavy and co-workers describe how (2R)-glyceryl-$\beta$-D-galactopyranoside can be synthesised from lactose and isopropylideneglycerol which are condensed to the corresponding galactoside by exposure to the $\beta$-galactosidase produced by *E. coli* and subsequently split by acid catalysis to the desired products. Similarly, T. Satoh and co-workers describe in Chem. Pharm. Bull. 32 (1984), 1183–1187, the use of lactase from *Kleuromyces fragilis* for synthesis of a series of galactosides. These workers make use of aryl glucosides as starting material for an enzyme catalysed exchange reaction with compound ROH (wherein R was alkyl) for synthesizing a series of alkyl glucosides. It appears from this publication that principally the same reaction can be carried out with widely differing radicals R, and in this regard this prior art reaction may be considered antecedent to the method according to the invention.

BRIEF STATEMENT OF THE INVENTION

The present invention relates to the use of enzymes for synthesis of carbohydrates carrying at their C-1 position (aldoses) or C-2 position (ketoses) an epoxy group. It has thus surprisingly been found that molecules carrying a highly reactive epoxy group can be used in enzymatic reactions and that the epoxy group can be transferred to another organic molecule without disturbing or inactivating the enzyme in spite of the fact that enzyme molecules contain numerous functional groups known to react with epoxides.

DISCUSSION OF THE INVENTION

Thus, the method according to the invention for preparation of an epoxy substituted aldose or ketose sugar comprises subjecting a reaction mixture of an aldose or ketose sugar or a glucosilated aldose or ketose sugar and a hydroxylated or thiolated epoxide having thereon a free hydroxyl group or thiol group to an enzymatic transfer reaction by presence in said reaction mixture of a glycosidase capable of splitting a sugar in the C-1 position (aldose) or C-2 position (ketose), forming thereby an epoxide substituted glucosilated aldose or ketose sugar and then recovering the epoxide substituted aldose or ketose sugar from the reaction mixture.

This method is schematically shown below.

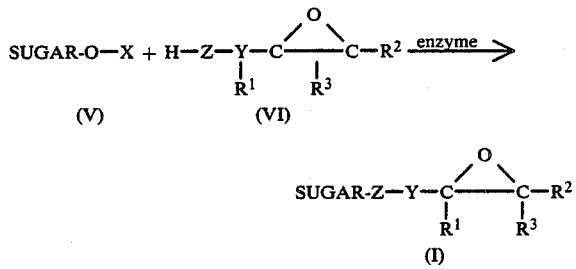

(V)    (VI)

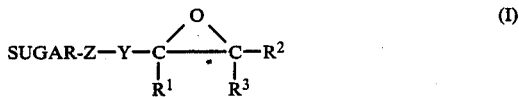

(I)

Thus, SUGAR is an aldose or a ketose, preferably a low molecular aldose or ketose, e.g. a mono-, di- or trisaccharide.

Also, Y, $R^1$, $R^2$, and $R^3$ are each any radical which does not inhibit the enzyme, which does not generate insolubility of a reactant or which does not prevent the transfer reaction by steric hindrance.

Also, X is a non interfering blocking group.

PREFERRED EMBODIMENTS

In a preferred embodiment of the method acccording to the invention for preparation of compounds of the general formula I

(I)

wherein SUGAR represents an aldose or ketose moiety, Z represents oxygen or sulphur attached to the terminal anomeric C-1 carbon atom (aldoses) or C-2 carbon atom (ketoses) of the sugar moiety, Y represents alkylene which may be substituted with hydroxy, mercapto, nitro, alkoxy, carboxy or amino, and $R^1$, $R^2$ and $R^3$ are the same or different, each representing hydrogen, alkyl or aryl, whereby both of the latter may be substituted with hydroxy, mercapto, nitro, alkoxy, carboxy or amino, this method is characterized by the fact that a compound of the general formula V

SUGAR—O—X    (V)

wherein SUGAR is as defined above, and X is hydrogen, a carbohydrate residue, alkyl or aryl all of which may be substituted with hydroxy, mercapto, nitro, alkoxy, carboxy or amino, is reacted with a compound of the general formula VI

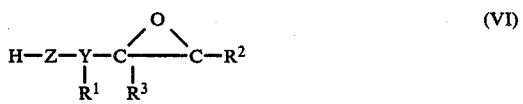
(VI)

wherein $R^1$, $R^2$, $R^3$, Y and Z each are as defined above, whereby the reaction is catalyzed by an enzyme, which is able to split the moiety SUGAR—O— at the position indicated by the arrow: Sugar⊥O—.

Thus, if SUGAR is the α-glucose moiety, the enzyme to be used is α-glucosidase, if SUGAR is the β-maltose moiety, the enzyme to be used is β-maltosidase, etc. It is to be understood that these enzymes do not exhibit a splitting activity only, but also a corresponding transfer activity in regard to the same site as the splitting site.

The aldose or ketose moiety corresponding to the radical SUGAR ordinarily is ribose, xylose, arabinose, mannose, galactose, glucose, fructose, lactose, cellobiose, maltose, or raffinose.

Thus, a defined SUGAR radical in this invention can always be associated with an enzyme with a defined activity, as appears from that below indicated table, which is of an illustrative nature only. It is to be understood that for some SUGAR radicals a glycosidase with a relatively unspecific activity will be able to catalyze the reaction, whereas in other cases more specific glycosidases are needed.

| SUGAR | Glycosidase activity |
|---|---|
| ribose | ribosidase |
| xylose | xylosidase |
| arabinose | arabinosidase |
| mannose | mannosidase |
| β-galactose | β-galactosidase |
| glucose | glucosidase |
| fructose | fructosidase |
| lactose | lactase |
| cellobiose | cellobiase |
| maltose | maltase |

If any of the radicals Y, $R^1$, $R^2$, $R^3$, or X are substituted with an OH group or an SH group, these groups are preferably protected in a manner known per se in order to avoid excessive formation of by-products.

In a preferred embodiment of the method according to the invention SUGAR is β-galactose and the enzyme is a β-galactosidase, preferably produced by means of E. coli. Both the β-galactose and the β-galactosidase are easily available substances, and the end product is a valuable raw material for reaction with organic acids.

In a preferred embodiment of the method according to the invention the compound of formula V is lactose and the enzyme is galactosidase. Both lactose and galactosidase are cheap and readily available.

In a preferred embodiment of the method according to the invention the compound of formula V is sucrose, and the enzyme is glucosidase. Both sucrose and glucosidase are cheap and readily available.

In a preferred embodiment of the method according to the invention X is an aryl group with 6–10 carbon atoms. In this manner a very reactive substrate is made available.

In a preferred embodiment of the method according to the invention Z is oxygen, Y is methylene, and $R_1$, $R_2$ and $R_3$ are hydrogen. No steric hindrances are present, and the reaction can be carried out smoothly and in high yields.

In a preferred embodiment of the method according to the invention the enzyme is immobilized. In this manner all the usual advantages by using an immobilized enzyme are established.

In a preferred embodiment of the method according to the invention the reaction is carried out in an organic solvent. When both reactants are sparingly soluble in aqueous media, this embodiment is preferred.

In a preferred embodiment of the method according to the invention the process is carried out in a mixture of water and an organic solvent. When both reactants are sparingly soluble in purely aqueous media, but easily soluble in a mixture of water and an organic solvent, this embodiment is preferred.

In a preferred embodiment of the method according to the invention the method is carried out in a two-phase system. When one reactant is easily soluble in an aqueous medium and the other reactant is easily soluble in an organic solvent, this embodiment is preferred and the reaction takes place at the interphase.

The reactions which can be performed by the method according to this invention can be summarized as indicated in Scheme 3 wherein X is hydrogen, a carbohydrate residue, alkyl or aryl, all of which may be substituted with hydroxy, mercapto, nitro, alkoxy, carboxy or amino, Z is oxygen or sulphur, Y is alkylene which may be substituted with hydroxy, mercapto, nitro, alkoxy, carboxy or amino, and wherein $R^1$, $R^2$ and $R^3$ are the same or different each representing hydrogen, alkyl or aryl, whereby both of the latter may be substituted with hydroxy, mercapto, nitro, alkoxy, carboxy or amino, whereby the (unsubstituted) alkyl group preferably contains 6 carbon atoms or less than 6 carbon atoms, and whereby the (unsubstituted) aryl group preferably contains between 6 and 10 carbon atoms, inclusive.

Preferably, the alkylene group contains 8 carbon atoms or less than 8 carbon atoms, more preferably 4 carbon atoms or less than 4 carbon atoms. Examples of preferred carbohydrate residues (X) are monosaccharide residues, for example, a glucose residue. Preferably, aryl is phenyl or naphthyl, which can be substituted or unsubstituted. The substituted phenyl or naphthyl radicals are preferred, e.g. the nitro substituted radicals, due to the higher reactivity of the compound V. Preferably SUGAR is a monosaccharide, disaccharide, or trisaccharide residue and examples of such groups are a glucosyl, galactosyl and mannosyl residue.

The enzymes which can be used in the method according to the invention are enzymes capable of splitting the —OX bond of the substrate molecule of formula V. This class of enzymes comprises carbohydrases such as amyloglucosidases and lactases as well as galactosidases, invertases and glucosidases. The enzymes used in this invention may be in solution of immobilized. Also, the enzymes may be modified by chemical or genetic methods in order to optimize its reactivity in regard to the reaction in question.

The method according to the invention can be carried out simply by mixing the acceptor and donor component of the reaction, i.e. the compounds of formula V and VI, respectively, in water containing the enzyme at room temperature. If desired, the reaction mixture can be heated in order to accelerate the reaction. Also, organic solvents may be added to the reaction mixture in order to increase the solubility of the reactants and the pH value of the reaction medium may be adjusted in order to obtain maximum enzyme activity and/or stability.

The compounds of the general formula I which can be prepared by means of the method according to the invention can be used for many purposes. For example, the reactive epoxy group in molecules of the general formula I makes their coupling to other molecules possible. Therefore, sugar moieties can be easily transferred, for example, to a matrix carrying hydroxy groups such as Sepharose or cellulose, or sugar residues may be coupled to proteins which are thereby transformed into glycoproteins.

A reaction of special interest which can be carried out according to the process of this invention is illustrated below

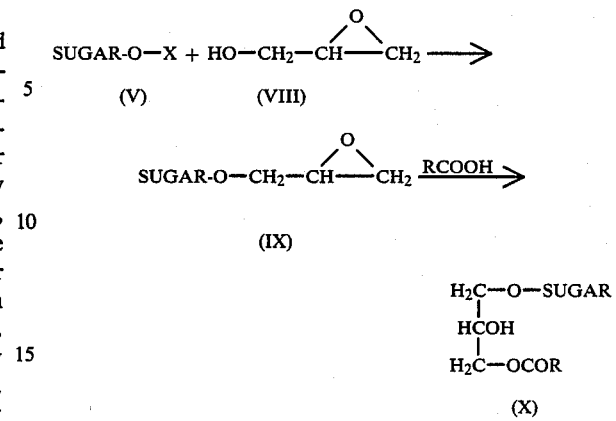

where R represents a carboxylic acid residue, for example alkyl, and SUGAR and X each are as has been defined.

As indicated, by exposure to the epoxide of formula VIII a substrate molecule of the general formula V can be converted to the epoxidated compound of formula IX which, as indicated, by reaction with a fatty acid can be transformed further to the monoglyceride of formula X. The compounds of the general formula X which can thus be made from compounds of the general formula IX by the process of this invention are surface active agents of great utility. These compounds may thus be used in food and feed as emulsifying agents, or they can be used to improve many functional properties of foods and feeds. Comparably, the reactive compounds of the general formula IX can also be coupled to amino acids, for example in proteins, thereby changing their functional properties.

The method according to the invention is illustrated by the following Examples 1 and 2, which however, are to be considered as illustrative of the invention only. Examples 3, 4, and 5 illustrate the application of the epoxy compounds produced by means of the invention.

EXAMPLE 1

Preparation of 2,3-epoxypropyl-β-D-galactopyranoside

β-Galactosidase (supplied by Boehringer Mannheim and derived from *E. coli*, 830 μl, about 50 U, suspended in $(NH_4)_2SO_4$) was added to a mixture of 5 g (16.6 mmol) of o-nitrophenylgalactopyranoside and 17.5 ml (0.26 mmol) of 2,3-epoxy-1-propanol in 400 ml of buffer (0.07M phosphat buffer, 10 mM $MgCl_2$, pH=7). The reaction was followed by thin layer chromatography (hereinafter designated TLC) and high pressure liquid chromatography (hereinafter designated HPLC). After 4 hours, the mixture was extracted with ether (4×100 ml) to remove nitrophenol and the water phase was evaporated at reduced pressure. The product was taken up in ethanol and filtered free from inorganic salts. Evaporation yielded 6.4 g crude product. This product was subject to chromatography on $SiO_2$ and further crystallized from absolute ethanol yielding 1.1 g (28%) of product. Melting point: 126°–127° C.

'H NMR(DMSO-d$^6$) delta; 2.6 (m, 1H), 2.74 (m, 1H), 3.14 (m, 1H), 3.2–3.4 (m, 3H), 3.45–3.55 (m, 2H), 3.56–3.65 (m, 2H), 3.73 (dd, 1H), 4.13 (d, 1H), 4.38 (d, 1H), 4.56 (m, 1H), 4.72 (d, 1H), 4.94 (d, 1H).

$^{13}$C NMR(DMSO-d$^6$) delta; 43.8, 50.1, 60.5, 68.2, 69.3, 70.5, 73.4, 75.2, 103.4.

EXAMPLE 2

Preparation of 2,3-epoxypropyl-β-D-galactopyranoside

β-Galactosidase (supplied by Boehringer Mannheim and derived from *E. coli*, 12 mg freeze dried, about 2400 U) was added to a mixture of 5 g (13.9 mmol) of lactose and 20 ml (0.3 mol) of 2,3-epoxy-1-propanol in 300 ml of buffer (0.07M phosphate buffer, 10 mM MgCl$_2$, pH=7). The reaction mixture was stirred for 15 hours at room temperature and subsequently heated to 80° C. for 10 minutes. The water phase was evaporated at reduced pressure. The product was taken up in ethanol and filtered free from inorganic salts. Evaporation yielded the crude product as a yellow sirup. Further purification was made analogous as described in Example 1 and the data were consistent with those given above.

EXAMPLE 3

Preparation of 1-O-tetradecanoyl-3-O-β-D-galactopyranosylglycerol 2,3-Epoxypropyl-β-D-galactopyranosid (1 g, 4.2 mmol) was added to myristic acid (1.06 g, 1.1 equivalent) at 80° C. Then, tetraethylammonium bromide (40 mg, 0.05 milli equivalent) was added. The semisolid mixture was stirred for 3 hours. The product was taken up in diethylketone/methanol (hereinafter designated Et$_2$O-MeOH) (50:50) and evaporated on SiO$_2$ followed by chromatography yielding 1.2 g (61%). The product was crystalized from acetone.

$^1$H NMR(DMSO-d$^6$) delta; 0.88 (t, 3H), 1.25 (bs, 20H), 1.54 (m, 2H), 2.32 (t, 2H), 3.25–3.6 (mm, 6H), 3.65 (bs, 1H), 3.72 (dd, 1H), 3.83 (m, 1H), 4.0 (m, 1H), 4.08 (m, 2H), 4.4 (d, 1H), 4.6 (t, 1H), 4.75 (d, 1H), 4.9 (d, 1H), 5.0 (d, 1H).

$^{13}$C NMR(DMSO-d$^6$) delta; 13.8, 22.0, 24.4, 28.5, 28.6, 28.7, 28.8, 28.9–29.0 (4c), 31.2, 33.5, 60.4, 65.4, 67.5, 68.1, 70.4, 70.6, 73.4, 75.3, 104.0, 172.8.

EXAMPLE 4

Preparation of 1-O-hexadecanoyl-3-O-β-D-galactopyranosylglycerol was performed similarly to Example 3

$^1$H NMR(DMSO-d$^6$) delta; 0.86 (t, 3H), 1.25 (bs, 24H), 1.5 (m, 2H), 2.3 (t, 2H), 3.25–3.55 (mm, 6H), 3.62 (bs, 1H), 3.7 (m, 1H), 3.8 (m, 1H), 3.96 (m, 1H), 4.05 (m, 2H), 4.4 (d, 1H), 4.55 (t, 1H), 4.7 (d, 1H), 4.85 (bs, 1H), 4.98 (d, 1H).

$^{13}$C NMR(DMSO-d$^6$) delta; 13.8, 22.0, 24.4, 28.5, 28.7 (2c), 28.9 (2c), 29.0 (5c), 31.2, 33.5, 60.4, 65.4, 67.5, 68.1, 70.4, 70.6, 73.4, 75.3, 104.0, 172.8.

EXAMPLE 5

Preparation of 1-O-octadecanoyl-3-O-β-D-galactopyranosylglycerol was performed similarly to Example 3

$^1$H NMR(DMSO-d$^6$) delta; 0.84 (t, 3H), 1.24 (bs, 28H), 1.5 (m, 2H), 2.28 (t, 2H), 3.25–3.55 (mm, 6H), 3.6 (bs, 1H), 3.68 (m, 1H), 3.8 (m, 1H), 3.95 (m, 1H), 4.05 (m, 2H), 4.35 (d, 1H), 4.55 (t, 1H), 4.7 (d, 1H), 4.85 (d, 1H), 4.95 (d, 1H).

$^{13}$C NMR(DMSO-d$^6$) delta, 13.8, 22.0, 24.4, 28.5, 28.6, 28.7, 28.9, 29.0 (8c), 31.3, 33.5, 60.4, 65.4, 67.5, 68.2, 70.5, 70.7, 73,4, 75.3, 104.0, 172.8.

We claim:

1. Method for preparation of an epoxy substituted aldose or ketose sugar which comprises subjecting a reaction mixture of an aldose or ketose sugar or a glucosilated aldose or ketose sugar and a hydroxylated or thiolated epoxide having thereon a free hydroxyl group or thiol group to an enzymatic transfer reaction by presence in said reaction mixture of a glycosidase capable of splitting a sugar in the C-1 position (aldose) or C-2 position (ketose), forming thereby an epoxide substituted glucosilated aldose or ketose sugar and then recovering the epoxide substituted aldose or ketose sugar from the reaction mixture.

2. Method for preparation of compounds of the general formula I

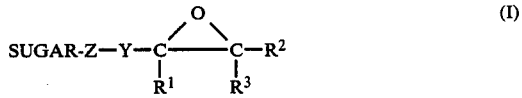

wherein SUGAR represents an aldose or ketose moiety, Z represents oxygen or sulphur attached to the terminal anomeric C-1 carbon atom of an aldose moiety or C-2 carbon atom of a ketose moiety, Y represents alkylene or substituted alkylene and R$^1$, R$^2$ and R$^3$ constitute non-interfering substituents wherein a compound of the general formula

SUGAR—O—X wherein SUGAR is as defined above, and X is a non-interfering substituent, is reacted with a compound of the general formula

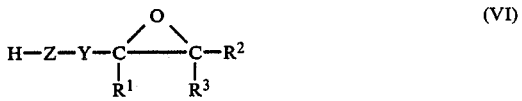

wherein R$^1$, R$^2$, R$^3$, Y and Z each are as defined above, in the presence of an enzyme, which is able to split the moiety SUGAR$\xrightarrow{}$O— at the position indicated by the arrow.

3. Method according to claim 2, wherein SUGAR is Beta galactose and the enzyme is a Beta galactosidase.

4. Method according to claim 2, wherein the compound SUGAR—O—X is lactose, and the enzyme is galactosidase.

5. Method according to the claim 2 wherein the compound SUGAR—O—X is sucrose, and the enzyme is glucosidase.

6. Method according to any one of the claim 2 wherein X is an aryl group with 6–10 carbon atoms.

7. Method according to claim 2 wherein Z is oxygen, Y is methylene, and R$^1$, R$^2$, and R$^3$, each is hydrogen.

8. Method according to claim 1 wherein the enzyme is immobilized.

9. Method according to claim 1 wherein the reaction is carried out in an organic solvent.

10. Method according to claim 1 wherein the process is carried out in a mixture of water and an organic solvent.

11. Method according to claim 1 wherein the process is carried out in a two-phase system.

* * * * *

UNITED STATES PATENT AND TRADEMARK OFFICE
CERTIFICATE OF CORRECTION

PATENT NO. : 4,859,589

DATED : August 22, 1989

INVENTOR(S) : Sven Erik Godtfredsen et al

It is certified that error appears in the above-identified patent and that said Letters Patent is hereby corrected as shown below:

Col. 2, line 34, "compound" should read -- compounds --.

Col. 4, line 5, "that" should read -- the --.

Col. 5, line 39, "of" should read -- or --.

Col. 5, line 68, "below" should read -- below. --

Col. 7, line 27, "milli equivalent" should read -- milliequivalent --.

Col. 7, line 66, "73,4" should read -- 73.4 --.

Col. 8, line 53, "any one of the" should be deleted.

Signed and Sealed this

Eleventh Day of September, 1990

*Attest:*

HARRY F. MANBECK, JR.

*Attesting Officer*     *Commissioner of Patents and Trademarks*